(12) United States Patent
McGinley et al.

(10) Patent No.: US 12,159,713 B2
(45) Date of Patent: Dec. 3, 2024

(54) SMART ORTHOPEDIC INSTRUMENT WITH AR DISPLAY

(71) Applicant: McGinley Engineered Solutions. LLC, Casper, WY (US)

(72) Inventors: Joseph C. McGinley, Casper, WY (US); Adam M. Johnson, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 1036 days.

(21) Appl. No.: 17/109,402

(22) Filed: Dec. 2, 2020

(65) Prior Publication Data

US 2021/0174956 A1 Jun. 10, 2021

Related U.S. Application Data

(60) Provisional application No. 62/944,914, filed on Dec. 6, 2019.

(51) Int. Cl.
| | |
|---|---|
| *G16H 40/67* | (2018.01) |
| *A61B 90/00* | (2016.01) |
| *A61B 90/50* | (2016.01) |
| *G16H 20/40* | (2018.01) |
| *G16H 40/20* | (2018.01) |
| *G16H 40/40* | (2018.01) |

(52) U.S. Cl.
CPC .............. *G16H 40/67* (2018.01); *A61B 90/36* (2016.02); *G16H 20/40* (2018.01); *G16H 40/20* (2018.01); *G16H 40/40* (2018.01); *A61B 2090/062* (2016.02); *A61B 2090/066* (2016.02); *A61B 2090/365* (2016.02); *A61B 2090/372* (2016.02); *A61B 2090/502* (2016.02)

(58) Field of Classification Search
CPC ........ G16H 40/67; G16H 40/20; G16H 40/40; G16H 20/40; A61B 90/36; A61B 2090/062; A61B 2090/365; A61B 2090/372; A61B 2090/066; A61B 2090/502; A61B 2034/2048; A61B 2034/254
USPC ..................... 345/418; 606/34, 130; 382/131
See application file for complete search history.

(56) References Cited

U.S. PATENT DOCUMENTS

| | | | |
|---|---|---|---|
| 11,864,728 B2 * | 1/2024 | Shelton, IV | A61B 5/0075 |
| 2004/0073279 A1 * | 4/2004 | Malackowski | A61B 90/98 |
| | | | 607/88 |
| 2013/0038707 A1 * | 2/2013 | Cunningham | H04N 7/183 |
| | | | 382/131 |
| 2015/0332196 A1 * | 11/2015 | Stiller | G16H 20/40 |
| | | | 705/2 |
| 2016/0287337 A1 * | 10/2016 | Aram | A61B 34/10 |

(Continued)

*Primary Examiner* — Prabodh M Dharia
(74) *Attorney, Agent, or Firm* — HOLZER PATEL DRENNAN

(57) ABSTRACT

A surgical imaging system for presenting one or more operational parameters to a user in an augmented reality display disposed in a user's field of vision. The one or more operational parameters may be derived from or include signals from one or more sensors of a smart surgical instrument. The augmented reality display may comprise a transparent or semitransparent display positioned between the user and the surgical field such that the user may look through the augmented reality display to view the surgical field. In this regard, a user may observe the one or more operational parameters without diverting attention from the surgical field.

20 Claims, 5 Drawing Sheets

(56) References Cited

U.S. PATENT DOCUMENTS

2017/0160549 A1\* 6/2017 Badiali ................ A61B 5/7445
2019/0201104 A1\* 7/2019 Shelton, IV ........... A61B 90/98

\* cited by examiner

SMART ORTHOPEDIC INSTRUMENT WITH AR DISPLAY

CROSS-REFERENCE TO RELATED APPLICATIONS

This application claims the benefit of U.S. Provisional patent Application No. 62/944,914, filed on Dec. 6, 2019, entitled "SMART ORTHOPEDIC INSTRUMENT WITH AR DISPLAY", the entirety of which is incorporated herein by reference.

The present application is related to U.S. Pat. No. 6,665,948 filed 5 Sep. 2002 entitled "DRILL BIT PENETRATION MEASUREMENT SYSTEM AND METHOD;" U.S. Pat. No. 9,370,372 filed 4 Sep. 2013 entitled "DRILL BIT PENETRATION MEASUREMENT SYSTEM AND METHOD;" and U.S. Pat. No. 10,390,869 filed 27 Oct. 2016 entitled "TECHNIQUES AND INSTRUMENTS FOR PLACEMENT OF ORTHOPEDIC IMPLANTS RELATIVE TO BONE FEATURES;" each of which is specifically incorporated by reference for all that it discloses and teaches.

BACKGROUND

Advances in surgical technology have resulted in new smart surgical instruments capable of measuring one or more operational parameters regarding a surgical operation. For example, smart surgical instruments that have sensors capable of monitoring specific aspects of the surgery have been proposed. Sensors may monitor the operation of the surgical instrument to measure one or more operational parameters regarding the surgical instrument or a working tool portion of the surgical instrument during the surgery. Such information may be used in a variety of manners to improve surgical outcomes for patients.

In some contexts, providing the information regarding the operational parameters determined by the sensors to the surgeon in real time during an operation may be of particular benefit. For instance, this type of feedback may allow a surgeon to modify or control the operation of the surgical instrument based on data provided to the surgeon. However, currently contemplated methods for providing such data are inadequate and limit the potential benefit of providing such information. For example, current approaches may require a surgeon to divert their attention or focus away from the surgical field to remotely located monitors to observe information obtained from the sensors.

SUMMARY

In view of the foregoing, the present disclosure relates to improved surgical systems that provide visual feedback of operational parameters sensed by a smart surgical device by display of such information on an augmented reality display disposed within a surgeon's field of vision of the surgical field. Specifically, a surgical display system is provided that includes a smart surgical instrument. The smart surgical instrument has at least one sensor for monitoring at least one instrument operational parameter of the surgical instrument. A display controller is also provided that is in operative communication with the smart surgical instrument to receive data corresponding to at least one instrument operational parameter. The system also includes an augmented reality display positioned within a field of vision of an operator of the smart surgical instrument. The augmented reality display is controlled by the display controller to display information regarding the at least one instrument operational parameter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

BRIEF DESCRIPTIONS OF THE DRAWINGS

DETAILED DESCRIPTIONS

Figure 1:
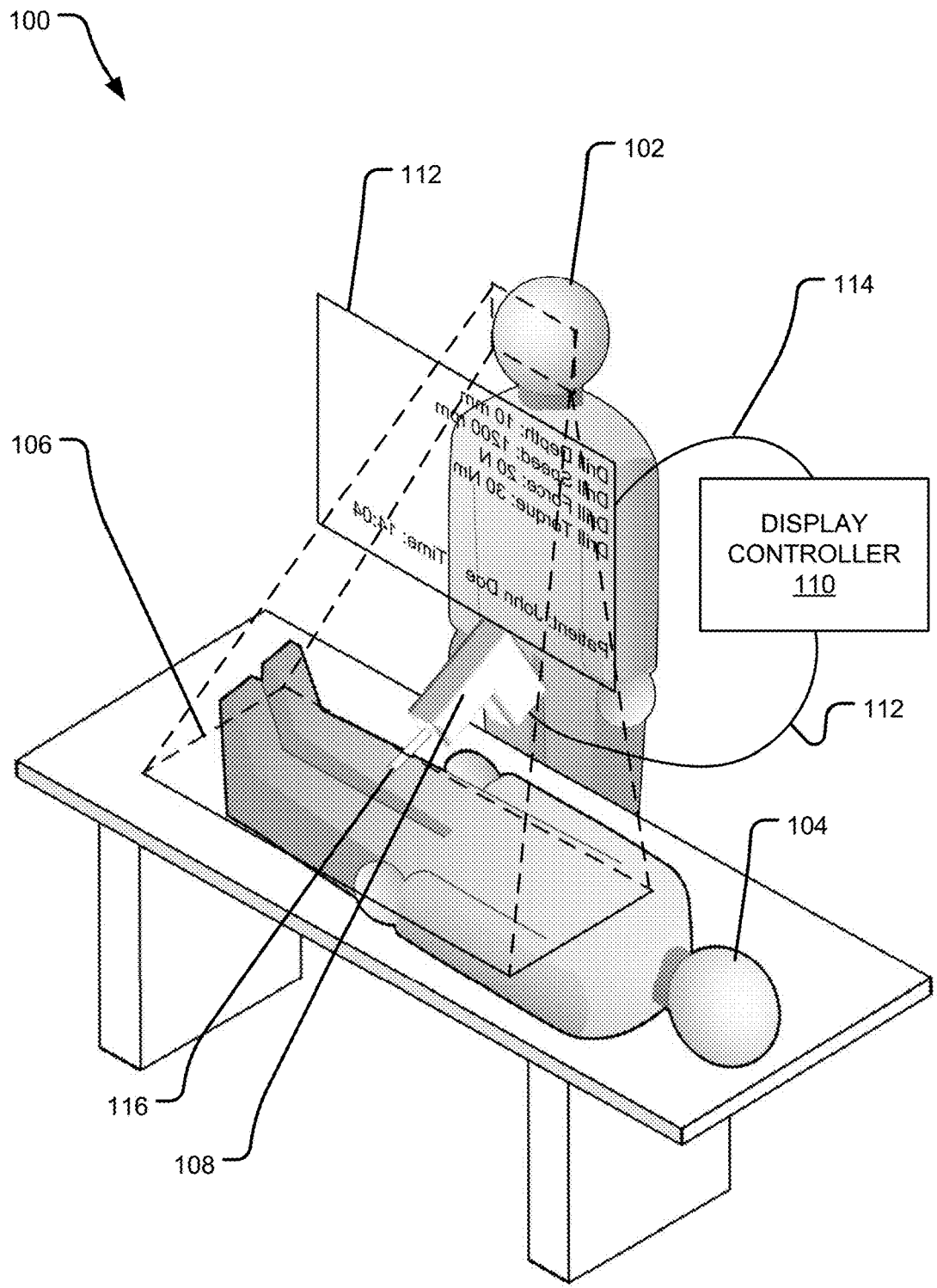
FIG. 1 depicts an example system in which information regarding at least one operational parameter is presented to a user of a smart surgical device using an augmented reality display disposed in a surgeon's field of vision.

FIG. 1 illustrates an example of a surgical display system 100. A user 102 (e.g., a surgeon) may utilize a smart surgical instrument 108 to operate on a patient 104. The user 102 may have a field of vision 106 that extends generally to an area of the patient 104 on which the operation is to be performed (e.g., the surgical field) using the smart surgical instrument 108.

While depicted as a drill form factor in FIG. 1, the smart surgical instrument 108 may be any appropriate surgical instrument without limitation. For example, the surgical instrument 108 may be a powered surgical instrument that utilizes electrical, pneumatic, hydraulic, or other power source to drive a working tool 116. The working tool 116 may be any appropriate tool including, for example and without limitation, a drill bit, a saw blade, a burr grinder, a reamer, a pin (e.g., an intramedullary (IM) pin), a wire (e.g., a Kirschner wire), a fastener driver, or any other appropriate instrument.

An augmented reality display 112 may be disposed within the field of vision 106 of the user 102. Additionally, the smart surgical instrument 108 may provide data to a display controller 110. The data provided to the display controller 110 may comprise data from or regarding one or more sensors that may monitor operational parameters of the smart surgical instrument 108. In turn, the display controller 110 may render the data from or regarding the one or more sensors to provider information regarding the operational parameters monitored by the sensors to the user 102. Specifically, the display controller 110 may be in operative communication with the augmented reality display 112 to present the information to the user 102 within the field of vision 106 of the user 102. In this regard, the user 102 may maintain their focus on the patient 104 (e.g., the user 102 may maintain their field of vision 106 within the surgical field) while performing the operation using the smart surgical instrument 108 while simultaneously being presented with relevant information regarding the operational parameters displayed on the augmented reality display 112.

Any appropriate sensor onboard or remote to the smart surgical instrument 108 may provide data to the display controller 110 for use in generating the operational parameter information to be provided to the user 102. Contemplated sensors include, but are not limited to, force sensors, displacement sensors, torque sensors, voltage sensors, current sensors, speed sensors, orientation sensors, temperature sensors, or other appropriate sensors. In this regard, the one or more operational parameters presented to the user may include data regarding or otherwise derived from any one or more of these sensors. For example, the operational parameter information presented to the user may include, but is not limited to, instrument displacement relative to a reference point, force applied to the working tool portion 116, torque applied to the working tool portion 116, instrument speed, instrument power consumption, rotational energy of the working tool portion 116, instrument temperature, instrument power consumption, working tool portion 116 acceleration, working tool portion 116 velocity, placement information regarding the working tool portion 116, bore depth of a bore created by the working tool portion 116 that penetrates completely or partially through a bone, or other operational parameters. The augmented reality display 112 may also display additional information not derived from the sensors on the smart surgical instrument 108 such as date and time, patient information, or the like.

In addition, the smart surgical instrument 108 may be operative to determine when a distal end portion of the working tool portion 116 passes from a first medium of a first density to a second medium of a second density. For example, one or more devices and/or approaches described in U.S. Pat. Nos. 6,665,948; 9,370,372; and/or 10,390,869; each of which are incorporated herein by reference, may be utilized. In any regard, upon determination that the distal end portion of the working tool portion 116 passes from the first medium the second medium, the user 102 may be notified of this occurrence by way of information presented on the augmented reality display 112. In addition, a bore length created by the working tool portion 116 upon determining the distal end portion of the working tool portion 116 passes from the first medium to the second medium may be presented to the user 102 in the augmented reality display 112.

The augmented reality display 112 may comprise any appropriate display that allows the user 102 to both be presented with the operational parameter information as well as maintain vision of the patient 104. For example, a transparent or semitransparent screen may be provided within the user's field of vision 106 on which the information may be rendered. The transparent or semitransparent screen may be positioned between the smart surgical instrument 108 and the user 102 such that the user's field of vision 106 extends through the transparent or semitransparent augmented reality 112 display. Rendering the information may include projecting the data onto the transparent or semitransparent screen or utilizing display technologies integrated into the screen. For instance, transparent or semitransparent media may include pixel fields that allow information to be presented relative to the transparent or semitransparent screen. In this regard, a user may continue to observe the surgical field through the augmented reality display 112 while also being present information regarding the operational parameters.

The smart surgical instrument 108 may have a communication link 112 with the display controller 110 to communicate the data to the display controller 110. The communication link 112 may comprise a wired connection or wireless connection (e.g. Wi-Fi, Bluetooth, Zigbee, etc.). Furthermore the display controller 110 may have a communication link 114 with the augmented reality display. The communication link 114 may also be a wired or wireless connection.

In an example, the smart surgical instrument 108 may include a display control input device (not shown). The display control input device may be manipulated by the user 102 while operating the surgical instrument 108. In addition, the display control input device may be used to affect the augmented reality display 112. For example, the display control input device may include a button, toggle switch, selector device, control pad, or other input device that may be manipulated by the user 102 (e.g., without removing a hand from the smart surgical instrument 102). In turn, the display control input device may be used to, for example, toggle the augmented reality display 112 on or off, modify the information displayed on the augmented reality display 112, and/or select the information to be displayed on the augmented reality display 112. For example, a user may cycle through different screens displayed on the augmented reality display 112 to present different information (e.g., in relation to different operations or phases of a given operation).

Figure 2:
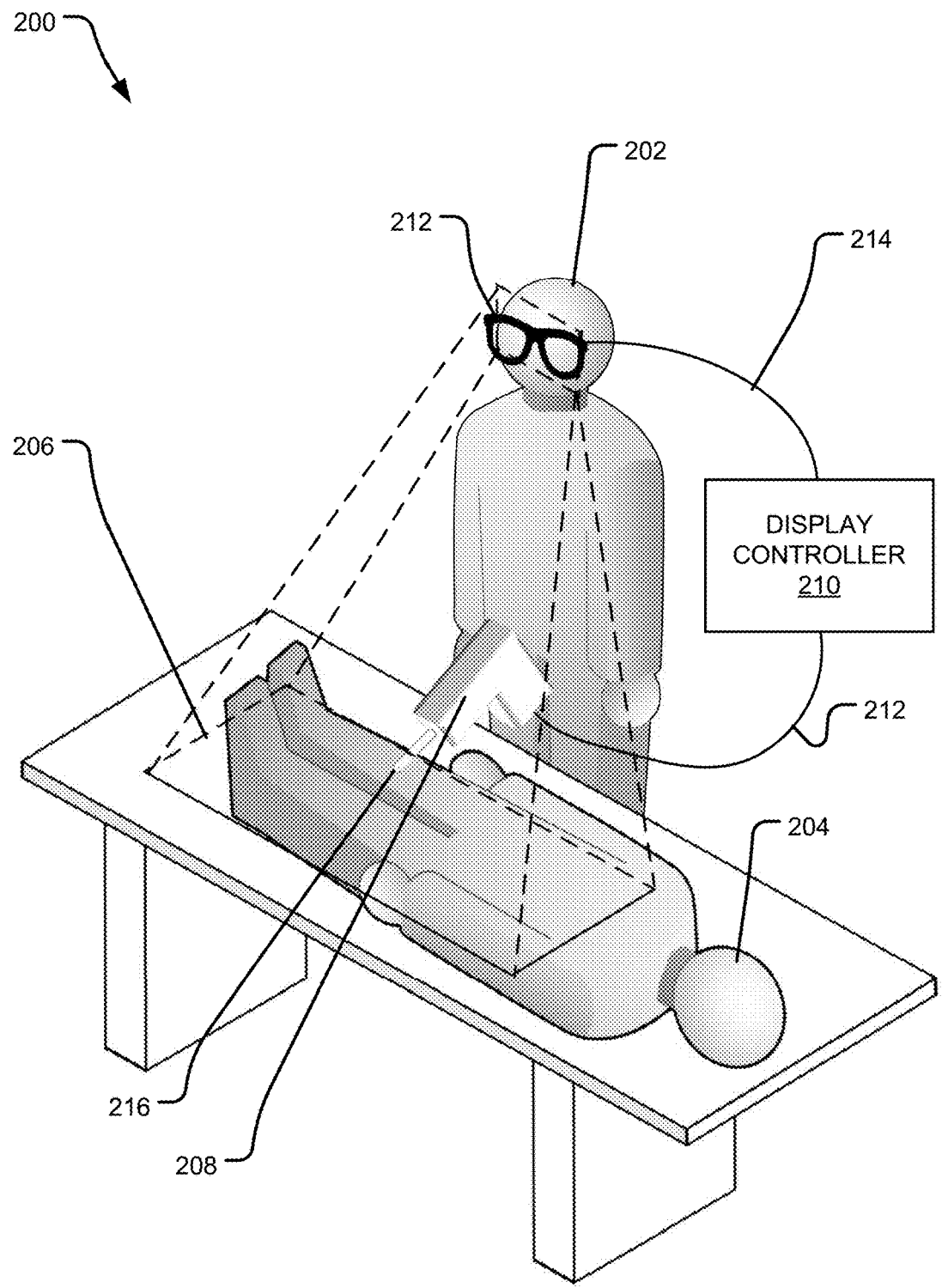
FIG. 2 depicts another example system in which information regarding at least one operational parameter is presented to a user of a smart surgical device using a wearable augmented reality display disposed in a surgeon's field of vision.

With further reference to FIG. 2, another example of a surgical display system 200 is shown. The system 200 may include a smart surgical instrument 208 that is manipulated by a user 202 within a field of vision of the user 202 to perform an operation on a patient 204. The smart surgical instrument 208 may communicate information to a display controller 210 over a communication link 212. In FIG. 2, the display controller 210 is in operative communication by way of a communication link 214 with an augmented reality headset display 212. The augmented reality headset display 212 may comprise a wearable display that the user 102 wears to position the augmented reality headset display 212 within the field of vision 206 of the user. The augmented reality headset display 212 may include smart glasses, smart goggles, a transparent face shield, a visor, or other appropriate form factor of the augmented reality headset display 212. In this regard, the wearable headset display 212 may comprise a transparent or semitransparent display portion that is disposed between the user 202 and the smart surgical instrument 208 such that the field of vision 206 of the user 202 extends through the wearable headset display 212 when observing the surgical field of the patient 204.

Figure 3:
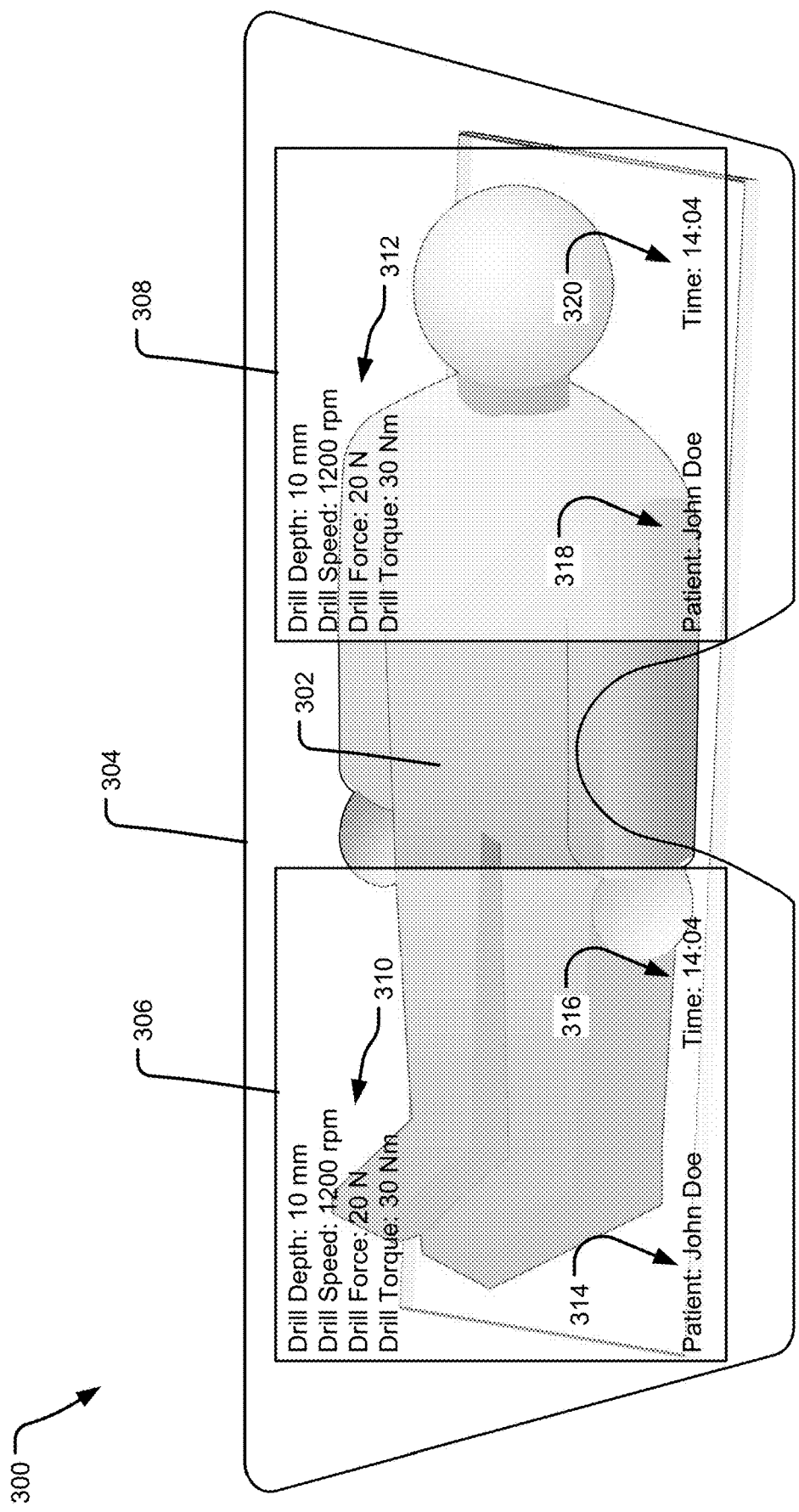
FIG. 3 depicts an example of a user's field of view through a wearable augmented reality display.

With further reference to FIG. 3, an example of a field of vision 300 of a user is illustrated. A augmented reality headset display 304 may be positioned within the user's field of vision 300 such that a patient 302 (e.g., a surgical field for the patient 302) may be within the field of vision 300 along with the augmented reality headset display 304. The augmented reality headset display 304 may include coordinating stereoscopic displays 306 and 308 to provide a unitary image presented to the user. For instance, the stereoscopic displays 306 and 308 may coordinate to present one or more operational parameters to the user. The stereoscopic displays 306 and 308 may coordinate to make it appear to the user that the displayed information is floating in the user's field of vision such that the information may be observed by the user while maintaining the patient 302 in the user's field of vision 300. In other embodiments, a single one of the displays 306 or 308 may be used to introduce the operational parameters into the field of vision 300 of the user.

The augmented reality headset display 304 may include a number of portions of information rendered on the display. For instance, one or more operational parameters 310 and 312 may be presented on the stereoscopic displays 306 and 308, respectively, to include drill depth, drill speed, drill force, and drill torque. However, any of the portions of information described above can be presented. For instance, patient information 314/318 and time information 316 and 320 are also displayed in FIG. 3.

Figure 4:
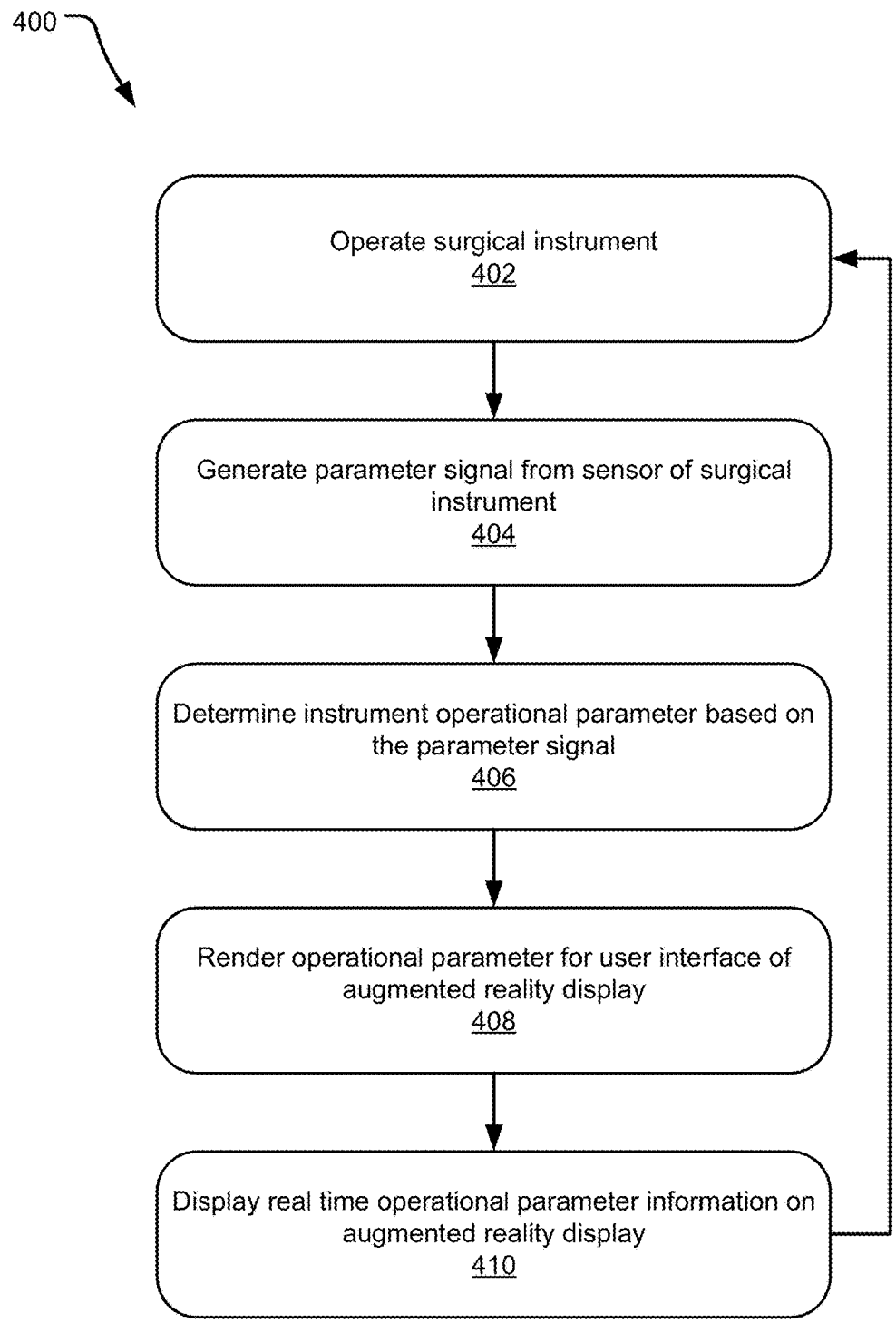
FIG. 4 depicts example operations of a method for displaying information regarding at least one operational parameter of a smart surgical instrument to a user.

FIG. 4 illustrates example operations 400 for display of operational parameters to a user using an augmented reality display. The example operations 400 include an operating operation 402 in which a smart surgical instrument is used to perform an operation. A generating operation 404 generates a parameter signal form a sensor of the smart surgical instrument. As described above, one or more sensors may be provided for monitoring the surgical instrument. Such sensors may be internal or external to the surgical instrument without limitation. In any regard, the operations 400 include a determining operation 406 to determine an instrument operational parameter based on the parameter signal from the generating operation 404. The determining operation 406 may be performed by the smart surgical instrument or a controller associated therewith. Alternatively, the determining operation 406 may be performed by a display controller to which the parameter signal or data related thereto (e.g., data derived therefrom) is provided. In any regard, a rendering operation 408 renders operational parameter information. In turn, a displaying operation 410 displays the operational parameter information on an augmented reality display presented within the user's field of vision. The displaying operation 410 may occur in real time or near real time such that the user may instantaneously monitor the operational parameter displayed in the displaying operation 402 while performing the operating operation 402. IN this regard, the example operations 400 may continuously cycle to provide updated (e.g., real-time) information to the user.

Figure 5:
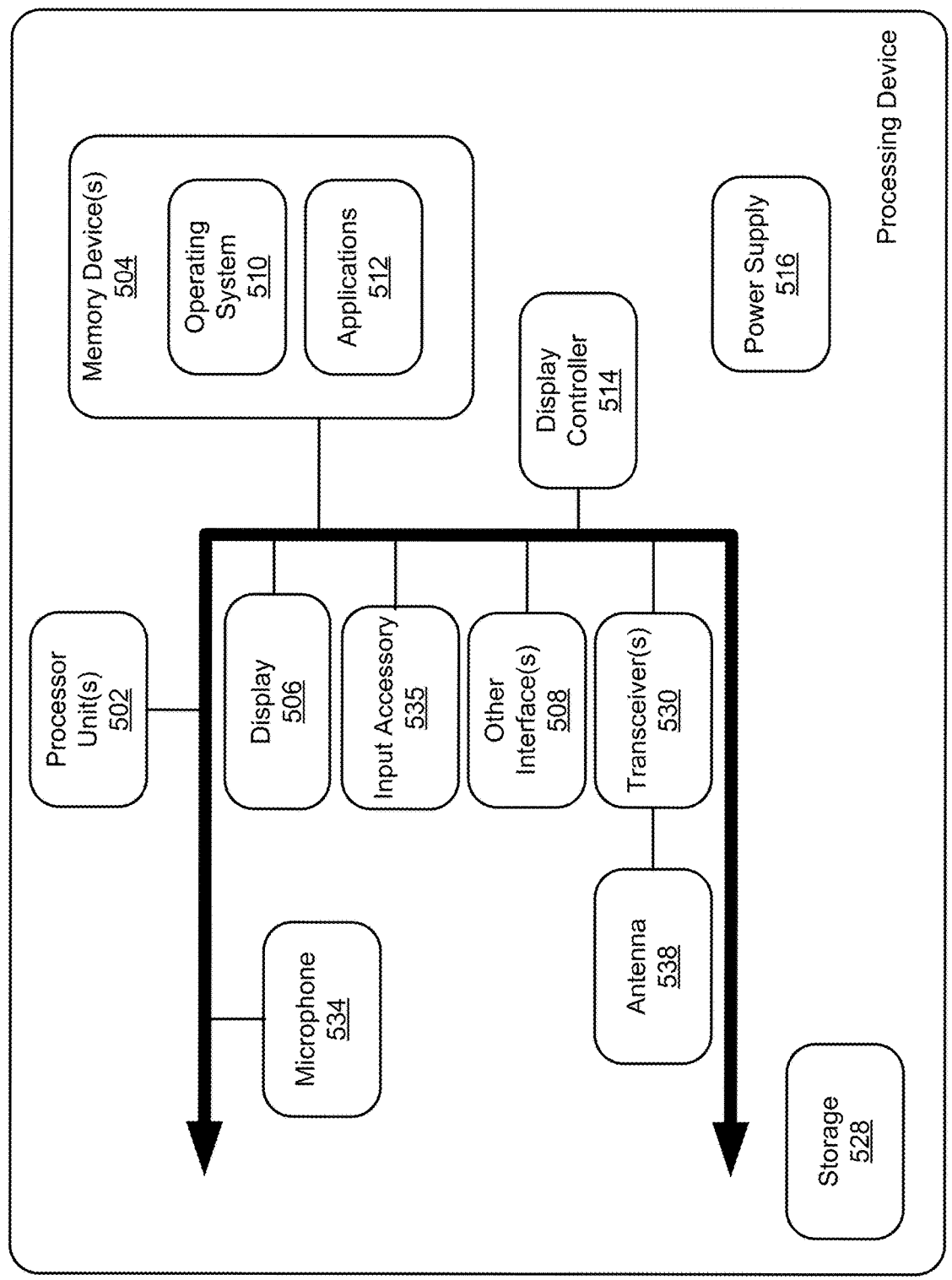
FIG. 5 depicts an example processing device that may facilitate certain aspects of the present disclosure.

FIG. 5 illustrates an example schematic of a processing device 500 suitable for implementing aspects of the disclosed technology including a display controller 514 as described above. The processing device 500 includes one or more processor unit(s) 502, memory 504, a display 506, and other interfaces 508 (e.g., buttons). The memory 504 generally includes both volatile memory (e.g., RAM) and non-volatile memory (e.g., flash memory). An operating system 510, such as the Microsoft Windows® operating system, the Apple macOS operating system, or the Linux operating system, resides in the memory 504 and is executed by the processor unit(s) 502, although it should be understood that other operating systems may be employed.

One or more applications 512 are loaded in the memory 504 and executed on the operating system 510 by the processor unit(s) 502. Applications 512 may receive input from various input local devices such as a microphone 534, input accessory 535 (e.g., keypad, mouse, stylus, touchpad, joystick, instrument mounted input, or the like). Additionally, the applications 512 may receive input from one or more remote devices such as remotely-located smart devices by communicating with such devices over a wired or wireless network using more communication transceivers 530 and an antenna 538 to provide network connectivity (e.g., a mobile phone network, Wi-Fi®, Bluetooth®). The processing device 500 may also include various other components, such as a positioning system (e.g., a global positioning satellite transceiver), one or more accelerometers, one or more cameras, an audio interface (e.g., the microphone 534, an audio amplifier and speaker and/or audio jack), and storage devices 528. Other configurations may also be employed.

The processing device 500 further includes a power supply 516, which is powered by one or more batteries or other power sources and which provides power to other components of the processing device 500. The power supply 516 may also be connected to an external power source (not shown) that overrides or recharges the built-in batteries or other power sources.

In an example implementation, a display system may include hardware and/or software embodied by instructions stored in the memory 504 and/or the storage devices 528 and processed by the processor unit(s) 502. The memory 504 may be the memory of a host device or of an accessory that couples to the host.

The processing device 500 may include a variety of tangible processor-readable storage media and intangible processor-readable communication signals. Tangible processor-readable storage can be embodied by any available media that can be accessed by the processing device 500 and includes both volatile and nonvolatile storage media, removable and non-removable storage media. Tangible processor-readable storage media excludes intangible communications signals and includes volatile and nonvolatile, removable and non-removable storage media implemented in any method or technology for storage of information such as processor-readable instructions, data structures, program modules or other data. Tangible processor-readable storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other tangible medium which can be used to store the desired information and which can be accessed by the processing device 500. In contrast to tangible processor-readable storage media, intangible processor-readable communication signals may embody processor-readable instructions, data structures, program modules or other data resident in a modulated data signal, such as a carrier wave or other signal transport mechanism. The term "modulated data signal" means an intangible communications signal that has one or more of its characteristics set or changed in such a manner as to encode information in the signal. By way of example, and not limitation, intangible communication signals include signals traveling through wired media such as a wired network or direct-wired connection, and wireless media such as acoustic, RF, infrared, and other wireless media.

Some implementations may comprise an article of manufacture. An article of manufacture may comprise a tangible storage medium to store logic. Examples of a storage medium may include one or more types of processor-readable storage media capable of storing electronic data, including volatile memory or non-volatile memory, removable or non-removable memory, erasable or non-erasable memory, writeable or re-writeable memory, and so forth. Examples of the logic may include various software elements, such as software components, programs, applications, computer programs, application programs, system programs, machine programs, operating system software, middleware, firmware, software modules, routines, subroutines, operation segments, methods, procedures, software interfaces, application program interfaces (API), instruction sets, computing code, computer code, code segments, computer code segments, words, values, symbols, or any combination thereof. In one implementation, for example, an article of manufacture may store executable computer program instructions that, when executed by a computer, cause the computer to perform methods and/or operations in accordance with the described implementations. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computer to perform a certain operation segment. The instructions may be implemented using any suitable high-level, low-level, object-oriented, visual, compiled and/or interpreted programming language.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

What is claimed is:

1. A surgical display system, comprising:
    a smart surgical instrument comprising a sensor for monitoring at least one instrument operational parameter of the surgical instrument, wherein the at least one instrument operational parameter is monitored during operation of the smart surgical instrument to provide information including data regarding or otherwise derived from the sensor;
    a display controller in operative communication with the smart surgical instrument to receive data corresponding to the at least one instrument operational parameter; and
    an augmented reality display positioned within a field of vision of an operator of the smart surgical instrument, the augmented reality display being controlled by the display controller to display information regarding the at least one instrument operational parameter.

2. The surgical display system of claim 1, wherein the augmented reality display comprises a wearable display worn by the operator to dispose the augmented reality display in the field of view of the operator.

3. The surgical display system of claim 2, wherein the smart surgical instrument comprises a display control input device for manipulation by the operator to affect the augmented reality display.

4. The surgical display system of claim 3, wherein the display control device is actuatable by the operator of the surgical instrument while using the surgical instrument to modify a display in the augmented reality display.

5. The surgical display system of claim 1, wherein the sensor comprises at least one of a torque sensor or a force sensor.

6. The surgical display system of claim 5, wherein the at least one instrument operational parameter comprises a working tool operational parameter regarding a working tool portion of the surgical instrument.

7. The surgical display system of claim 6, wherein the working tool operational parameter comprises at least one of a torque applied to the working tool portion, a force applied to the working tool portion, a rotational speed of the working tool portion, or a rotational energy measure of the working tool portion.

8. The surgical display system of claim 1, wherein the surgical instrument comprises a measurement system for measuring a depth of penetration of a working tool of the smart surgical instrument relative to a reference point.

9. The surgical display system of claim 8, wherein the at least one instrument operational parameter comprises a measurement parameter from the measurement system corresponding to the depth of penetration of a working tool of the smart surgical instrument relative to the reference point.

10. The surgical display system of claim 9, wherein the measurement system is operative to determine a distal end portion of the working tool passing through an interface between a first medium to a second medium and to determine the depth of penetration from the reference point to the interface, the display controller receiving the depth of penetration and displaying the depth of penetration on the augmented reality display in response to the distal end portion of the working tool passing through the interface.

11. A method for display of information related to a surgical instrument, comprising:
    operating a smart surgical instrument;
    generating a parameter signal regarding a sensor of the smart surgical instrument during the operating operation;
    determining at least one instrument operational parameter of the surgical instrument based on the parameter signal; and
    displaying information regarding the at least one instrument operational parameter in an augmented reality display positioned within a field of vision of an operator of the smart surgical instrument, wherein the at least one instrument operational parameter is monitored during operation of the smart surgical instrument to provide information including data regarding or otherwise derived from the sensor.

12. The method of claim 11, wherein the augmented reality display comprises a wearable display worn by the operator to dispose the augmented reality display in the field of view of the operator.

13. The method of claim 12, further comprising:
    receiving an input from a display control input device manipulated by the operator; and
    modifying the displayed information in response to the input.

14. The method of claim 13, wherein the input is received during the operating operation.

15. The method of claim 11, wherein the sensor comprises at least one of a torque sensor or a force sensor.

16. The method of claim 15, wherein the at least one instrument operational parameter comprises a working tool operational parameter regarding a working tool portion of the surgical instrument.

17. The method of claim 16, wherein the working tool operational parameter comprises at least one of a torque applied to the working tool portion, a force applied to the working tool portion, a rotational speed of the working tool portion, or a rotational energy measure of the working tool portion.

18. The method of claim 11, wherein the surgical instrument comprises a measurement system for measuring a depth of penetration of a working tool of the smart surgical instrument relative to a reference point.

19. The method of claim 18, wherein the at least one instrument operational parameter comprises a measurement parameter from the measurement system corresponding to the depth of penetration of a working tool of the smart surgical instrument relative to the reference point.

20. The method of claim 19, further comprising:
   determining that a distal end portion of the working tool passes through an interface between a first medium to a second medium;
   measuring, using the measurement system, the depth of penetration from the reference point to the interface; and
   displaying the depth of penetration on the augmented reality display in response to the distal end portion of the working tool passing through the interface.

* * * * *